(12) United States Patent
Fish et al.

(10) Patent No.: US 8,907,783 B2
(45) Date of Patent: Dec. 9, 2014

(54) MULTIPLE-APPLICATION ATTACHMENT MECHANISM FOR HEALTH MONITORING ELECTRONIC DEVICES

(75) Inventors: Ram David Adva Fish, Menlo Park, CA (US); Soroush Salehian Dardashti, Mountain View, CA (US)

(73) Assignee: Numera, Inc., Seattle, WA (US)

( * ) Notice: Subject to any disclaimer, the term of this patent is extended or adjusted under 35 U.S.C. 154(b) by 195 days.

(21) Appl. No.: 13/439,713

(22) Filed: Apr. 4, 2012

(65) Prior Publication Data

US 2012/0329292 A1 Dec. 27, 2012

Related U.S. Application Data

(60) Provisional application No. 61/516,477, filed on Apr. 4, 2011.

(51) Int. Cl.
| | |
|---|---|
| *G08B 21/00* | (2006.01) |
| *H01R 13/62* | (2006.01) |
| *A61B 5/00* | (2006.01) |
| *A61B 5/145* | (2006.01) |
| *A61B 5/021* | (2006.01) |
| *A61B 5/0402* | (2006.01) |

(52) U.S. Cl.
CPC ......... *H01R 13/6205* (2013.01); *A61B 5/14532* (2013.01); *A61B 5/021* (2013.01); *A61B 2562/0223* (2013.01); *H01R 2201/12* (2013.01); *A61B 2562/0219* (2013.01); *A61B 5/0402* (2013.01); *A61B 5/002* (2013.01)
USPC .......................................... 340/539.12; 439/39

(58) Field of Classification Search
USPC ............ 340/539.12, 500, 999; 439/38, 39, 40
See application file for complete search history.

(56) References Cited

U.S. PATENT DOCUMENTS

| | | | |
|---|---|---|---|
| 7,311,526 | B2 | 12/2007 | Rohrbach et al. |
| 7,658,613 | B1 * | 2/2010 | Griffin et al. ................... 439/39 |
| 7,841,776 | B2 | 11/2010 | DiFonzo et al. |
| 2008/0275349 | A1 * | 11/2008 | Halperin et al. .............. 600/484 |

* cited by examiner

*Primary Examiner* — Jeffrey Hofsass
(74) *Attorney, Agent, or Firm* — Lowenstein Sandler LLP (57) ABSTRACT

A portable computing device may include a set of magnetic elements and a set of electrical contacts. An electronic device may include a sensor may also include a set of magnetic elements and a set of electrical contacts. The portable computing device may attach to the electronic device using the set of magnetic elements and may exchange data with the electronic device using the set of electrical contacts. A power source may also include a set of magnetic elements and a set of electrical contacts. The power source may couple with the portable computing device using the set of magnetic elements and may provide power to the portable computing device using the electrical contacts.

20 Claims, 10 Drawing Sheets

MULTIPLE-APPLICATION ATTACHMENT MECHANISM FOR HEALTH MONITORING ELECTRONIC DEVICES

CROSS-REFERENCE TO RELATED APPLICATION

This application claims the benefit of U.S. Provisional Patent Application No. 61/516,477 filed Apr. 4, 2011, the disclosure of which is incorporated herein by reference in its entirety.

TECHNICAL FIELD

Embodiments of the present invention relate generally to health care-based monitoring systems, and more specifically, to a system and method for attaching sensors and other components to electronic devices.

BACKGROUND

For certain age groups, such as the elderly, or people that engage in certain dangerous activities, such as firefighters and soldiers, it is desirable to track and understand human activity automatically. For example, a person that has fallen may be injured, unconscious, etc., and needs emergency assistance. In such circumstances, relying on the person to initiate a call to a public safety access point (PSAP) (e.g., 9-1-1 emergency services, an automated emergency call center, etc.) is not practical. Moreover, even if the person is capable of placing the call, the PSAP may be located outside the geographical jurisdiction for providing emergency services. An emergency services person located at a PSAP may need to manually place a second call to the local fire station, police, or Emergency Medical Services (EMS) squad, thereby wasting precious time that could be used to save the person's life. Further, if the person is unconscious, they would not be able to relate the nature of their injuries nor their physical location.

Portable computing devices such as smart phones, personal digital assistants (PDAs), cellular phones, media players, tablet computers, and electronic readers, are becoming more prevalent. Although these portable computing devices are used for a variety of purposes such as viewing digital media, connecting to social networks, placing phone calls, etc., these portable computing devices often do not perform health monitoring functions.

BRIEF DESCRIPTION OF THE DRAWINGS

Embodiments of present invention will be more readily understood from the detailed description of exemplary embodiments presented below considered in conjunction with the attached drawings.

DETAILED DESCRIPTION

Embodiments of the invention provide a portable computing device used by a user for automatically contacting a public safety access point (PSAP). The portable computing device includes several sensors for obtaining datasets. One of datasets includes a location of a user obtained from an aGPS receiver. The portable computing device also includes a cellular transceiver. The cellular transceiver transmits the datasets to a cloud computing system, receives emergency assistance instructions from the cloud computing system, and contacts a safety access point (PSAP) (e.g., 9-1-1 emergency services, an automated emergency call center, etc.) based on the location of the user.

In one embodiment, the portable computing device may include a set (e.g., one or more) of magnetic elements and a set of electrical contacts. A device attachable to the portable computing device, such as a health sensor or other device may also include a set of magnetic elements and a set of electrical contacts. The attachable device may be attached or coupled to the portable computing device using the sets of magnetic elements. In one embodiment, the set of magnetic elements on the portable computing device may be aligned with the set of magnetic elements on the attachable device and the set of electrical contacts on the portable computing device may be aligned with the set of electrical contacts on the attachable device. In another embodiment, a magnetic attraction between the sets of magnetic elements may maintain an electrical connection between the sets of electrical contacts. (e.g., may maintain the sets of electrical contacts in an electrically conductive relationship). In one embodiment, the attachable device may perform measurements, obtain data, or perform other functions, and may exchange data with the portable computing device using the electrical contacts. In another embodiment, the portable computing device may also provide power to the attachable device using one or more of the electrical contacts.

In one embodiment, the portable device may also couple or attach to a power source, using the set of magnetic elements and the set of electrical contacts on the portable device. The power source may also include a set of magnetic elements and a set of electrical contacts, which are aligned with the set of magnetic elements and set of electrical contacts on the portable computing device. In one embodiment, the power source may provide power to charge a battery on the portable computing device using one or more of the electrical contacts.

Figure 1:
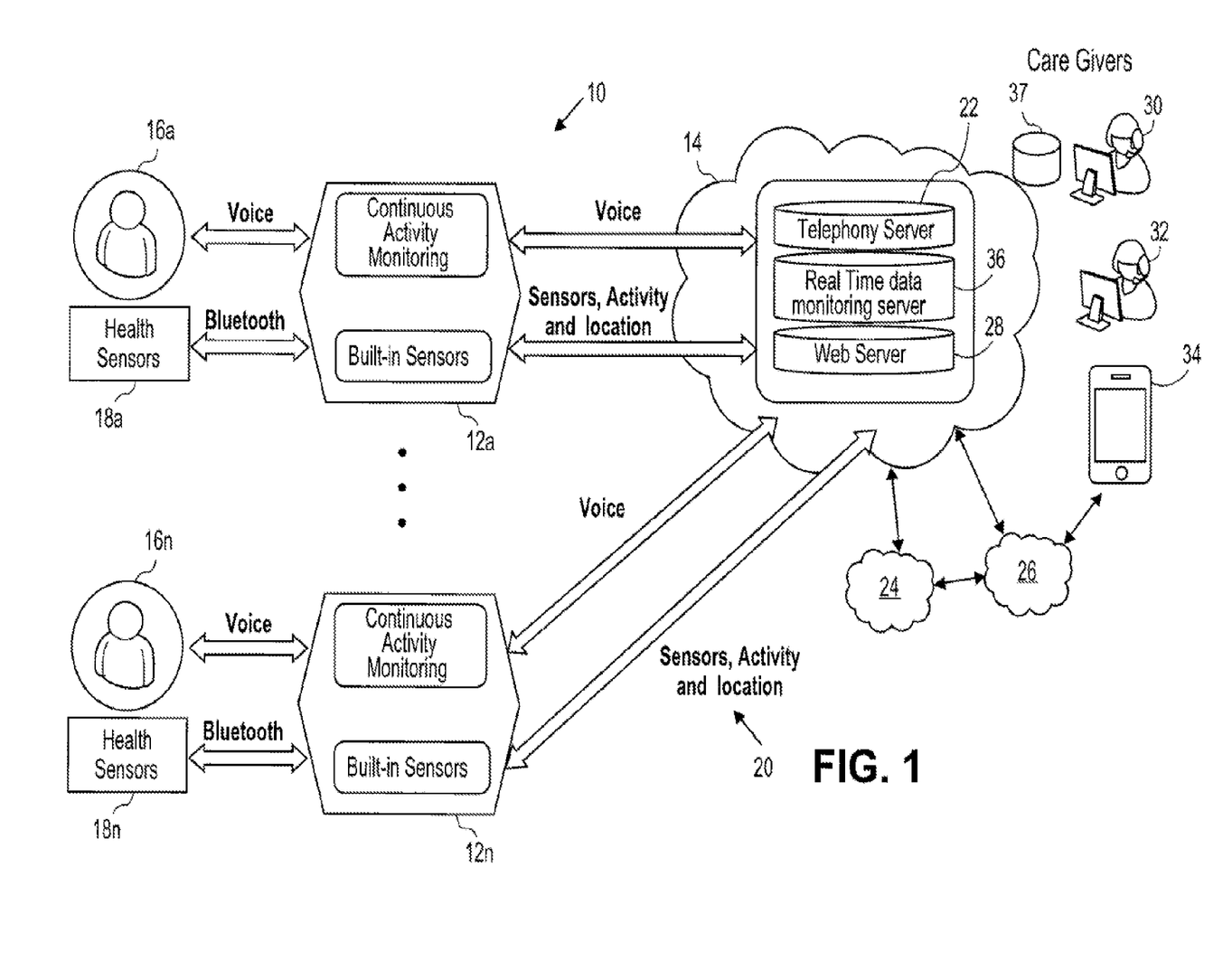
FIG. 1 is a block diagram illustrating one embodiment of a system for detecting a predefined user state.

FIG. 1 is a block diagram illustrating one embodiment of a system 10 for detecting a predefined user state. The system 10 includes portable computing devices 12a-12n communicatively connected to a distributed cloud computing system 14. A portable computing device 12 (e.g., a portable computing device) may be a small-size computing device that can be worn as a watch, a pendant, a ring, a pager, or the like, and can be held in any orientation.

In one embodiment, each of the portable computing devices 12a-12n is operable to communicate with a corresponding one of users 16a-16n (e.g., via a microphone, speaker, and voice recognition software), external health sensors 18a-18n (e.g., an EKG, blood pressure device, weight scale, glucometer) via, for example, a short-range over the air (OTA) transmission method (e.g., BlueTooth, WiFi, etc.), a call center 30, a first-to-answer system 32, and care giver and/or family member 34, and the distributed cloud computing system 14 via, for example, a long range OTA transmission method (e.g., over a $3^{rd}$ Generation (3G) or $4^{th}$ Generation (4G) cellular transmission network 20, such as a Long Term Evolution (LTE) network, a Code Division Multiple Access (CDMA) network, etc.).

Each portable computing device 12 is configured to detect a predefined state of a user. The predefined state may include a user physical state (e.g., a user fall inside or outside a building, a user fall from a bicycle, a car incident involving a user, a user taking a shower, etc.) or an emotional state (e.g., a user screaming, a user crying, etc.). As will be discussed in more detail below, the portable computing device 12 may include multiple sensors for detecting a predefined user state. For example, the wearable user device 12 may include an accelerometer for measuring an acceleration of the user, a magnetometer for measuring a magnetic field associated with the user's change of orientation, a gyroscope for providing a more precise determination of orientation of the user, and a microphone for receiving audio. Based on data received from the above sensors, the portable computing device 12 may identify a suspected user state, and then categorize the suspected user state as an activity of daily life, a confirmed predefined user state, or an inconclusive event. The wearable user device 12 may then communicate with the distributed cloud computing system 14 to obtain a re-confirmation or change of classification from the distributed cloud computing system 14. In another embodiment, the wearable user device 12 transmits data provided by the sensors to the distributed cloud computing system 14, which then determines a user state based on this data.

In one embodiment, the portable computing device 12 includes a low-power processor (e.g., low-power processing device) to process data receive from sensors and/or detect anomalous sensor inputs. The low-power processor may cause a second processing device to further analyze the sensor inputs (e.g., may wake up a main CPU and/or additional sensors). If the second processing device determines that there is possibly an anomalous event in progress the second processing device may send dataset to the distributed cloud computing system 14. In one embodiment, if the distributed cloud computing system 14 concludes there is an anomalous event, the distributed cloud computing system 14 may instruct the portable computing device 12 to initiate a voice call.

In one embodiment, the wearable user device 12 may also obtain audio data from one or more microphones on the portable computing device 12. For example, the wearable user device 12 may record the user's voice and/or sounds which are captured by the one or more microphones, and may provide the recorded sounds and/or voice to the distributed cloud computing system 14 for processing (e.g., for voice or speech recognition).

In one embodiment, the portable computing devices 12a-12n may continually or periodically gather/obtain data from the sensors and/or the one or more microphones (e.g., gather/obtain datasets and audio data) and the portable computing devices 12a-12n may transmit these datasets to the distributed cloud computing system 14. The datasets may be transmitted to the distributed cloud computing system 14 at periodic intervals, or when a particular event occurs (e.g., user pushes a button on the portable computing device 12a-12n or a fall is detected).

Cloud computing provides computation, software, data access, and storage services that do not require end-user knowledge of the physical location and configuration of the system that delivers the services. The term "cloud" refers to one or more computational services (e.g., servers) connected by a computer network.

The distributed cloud computing system 14 may include one or more computers configured as a telephony server 22 communicatively connected to the portable computing devices 12a-12n, the Internet 24, and one or more cellular communication networks 20, including, for example, the public circuit-switched telephone network (PSTN) 26. The distributed cloud computing system 14 may further include one or more computers configured as a Web server 28 communicatively connected to the Internet 24 for permitting each of the users 16a-16n to communicate with a call center 30, first-to-answer systems 32, and care givers and/or family 34. The web server 28 may also provide an interface for users to interact with the distributed cloud computing system 14 (e.g., to access their account, profiles, or subscriptions, to access stored datasets and/or audio data, etc.) The distributed cloud computing system 14 may further include one or more computers configured as a real-time data monitoring and computation server 36 communicatively connected to the portable computing devices 12a-12n for receiving measurement data (e.g., datasets), for processing measurement data to draw conclusions concerning a potential predefined user state, for transmitting user state confirmation results and other commands back to the portable computing devices 12a-12n, and for storing and retrieving present and past historical predefined user state data from a database 37 which may be employed in the user state confirmation process, and in retraining further optimized and individualized classifiers that can in turn be transmitted to the portable computing device 12a-12n.

In one embodiment, the portable computing devices 12a-12n may include a button, which a user 16 may use to initiate voice calls. For example, a user 16a may push the button on the device 12a to initiate a voice call in order to obtain assistance or help (e.g., because the user has slipped or fallen, or because the user requires medical assistance). As discussed above, the portable computing devices 12a-12n may periodically transmit datasets to the distributed cloud computing system 14. In one embodiment, the portable computing devices 12a-12n may also transmit datasets to the distributed cloud computing system 14 when the user press or pushes the button on the portable computing devices 12a-12n. In one embodiment, the portable computing devices 12a-12n may be single-button devices (e.g., devices which only have one button), which provide a simplified interface to users.

In one embodiment, the distributed cloud computing system 14 may receive a request from the portable computing device 12a-12n to initiate the voice call. The distributed cloud computing system 14 may also receive datasets from the portable computing device 12a-12n associated with an event experienced by the user. After receiving the request to initiate the voice call, the distributed cloud computing system 14 may analyze the datasets to determine whether the event experienced by the user is an activity of daily life, a confirmed fall, or an inconclusive event. In another embodiment, the distributed cloud computing system 14 may identify a destination for routing the voice call, based on the analysis of the datasets. For example, if the distributed cloud computing system 14 analyzes the datasets and determines that the event is a confirmed fall, the distributed cloud computing system 14 may identify a first-to-answer system 32 (e.g., a 911 or emergency response call center) as destination for the voice call. In another example, if the distributed cloud computing system 14 analyzes the datasets and is unable to determine what event occurred (e.g., an inconclusive event), the distributed cloud computing system 14 may identify a family member 24, as destination for the voice call. After identifying a destination for the voice call, the distributed cloud computing system 14 routes the voice call to the identified destination.

In one embodiment, the distributed cloud computing system 14 may also analyze audio data received from a portable computing device 12 to determine whether an event has happened to a user. For example, the portable computing device 12 may provide audio data (e.g., a recording of the user's voice or other sounds) to the distributed cloud computing system 14. The distributed cloud computing system 14 may analyze the sound data and may determine that a user is asking for help (e.g., based on the user's words, cries, and/or other sounds in the recording). The distributed cloud computing system 14 may identify a destination for the voice call, based on the audio data and/or the datasets received from the portable computing device 12 and may route the voice call to the identified destination. The audio data may be used in conjunction with the datasets to identify a destination for routing the voice call.

In another embodiment, the distributed cloud computing system 14 may monitor the status of the voice call, after it routes the voice call to the identified destination. For example, the distributed cloud computing system 14 may route the voice call to a family member 34. The distributed cloud computing system 14 may monitor the voice call and may determine that the family member 34 did not answer the voice call. The distributed cloud computing system 14 may then route the voice call to a second destination (e.g., to a call center 30), based on the status of the voice call (e.g., based on the voice call failing to connect at the first destination).

In one embodiment, the distributed cloud computing system 14 may also use subscription data (e.g., information associated with a user's account or subscription to a service) to identify destinations for routing the voice call. For example, a user may have a higher tier/level subscription which specifies that voice calls initiated by the user (via the button on the portable computing device 12) should be routed to a live person, such as a call center 30 or a first-to-answer system 32 (e.g. a 911 response center). In another example, a user may have a lower tier/level subscription which specifies that voice calls initiated by the user (via the button on the portable computing device 12) should be routed to family member 34 first, and then to a call center 30 if the family member 34 is not able to answer the voice call. The subscription data may be used in conjunction with the datasets and/or audio data to identify a destination for routing the voice call.

In a further embodiment, the distributed cloud computing system 14 may also use a time of day and/or a geographic location to identify destinations for routing a voice call. For example, if a request to initiate a voice call is received in the evening (e.g., 7:00 PM), the distributed cloud computing system 14 may route the voice call to a call center 30, but if a request to initiate a voice call is received during the morning (e.g., 10:30 AM), the distributed cloud computing system 14 may route the voice call to a family member 34. In a further example, the distributed cloud computing system 14 may determine that the portable computing device 12 (which is worn by the user 16) is not located within the home of the user 16, and may route the voice call to a call center 30. If the portable computing device 12 is located within the user's home, the distributed cloud computing system 14 may route the voice call to a family member 34. In one embodiment, the distributed cloud computing system 14 may route the voice call to a variety of destinations based on user preferences and/or based on a user's account/subscription level.

Figure 2:
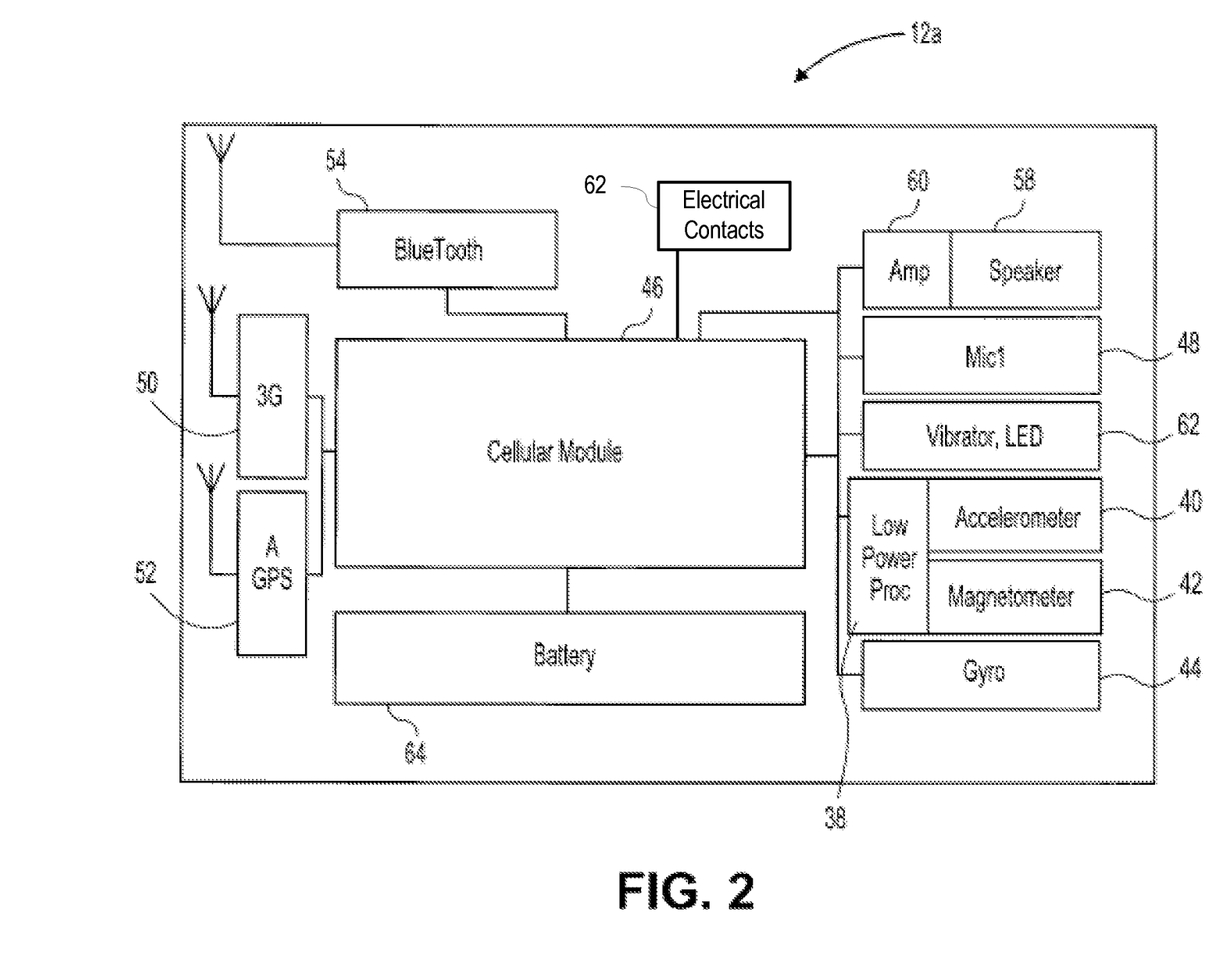
FIG. 2 is a block diagram illustrating one embodiment of a portable computing device.

FIG. 2 is a block diagram illustrating one embodiment of a portable computing device 12a (e.g., portable computing device 12a shown in FIG. 1). The portable computing device 12a may include a low-power processor 38 communicatively connected to an accelerometer 40 (e.g., a two- or more-axis accelerometer) for detecting acceleration events (e.g., high, low, positive, negative, oscillating, etc.), a magnetometer 42 (preferably a 3-axis magnetometer) for assessing an orientation of the portable computing device 12a, and a gyroscope 44 for providing a more precise determination of orientation of the portable computing device 12a. The low-power processor 38 is configured to receive continuous or near-continuous real-time measurement data from the accelerometer 40, the magnetometer 42, and the gyroscope 44 for rendering tentative decisions concerning predefined user states. By utilizing the above components, the portable computing device 12 is able to render these decisions in relatively low-computationally expensive, low-powered manner and minimize false positive and false negative errors. A cellular module 46, such as the 3G IEM 6270 manufactured by Qualcomm®, includes a high-computationally-powered microprocessor element and internal memory that are adapted to receive the suspected fall events from the low-power processor 38 and to further correlate orientation data received from the optional gyroscope 44 with digitized audio data received from one or more microphones 48 (preferably, but not limited to, a micro-electro-mechanical systems-based (MEMS) microphone(s)). The audio data may include the type, number, and frequency of sounds originating from the user's voice, the user's body, and the environment.

The cellular module 46 is also configured to receive commands from and transmit data to the distributed cloud computing system 14 via a 3G, 4G, and/or other wireless protocol transceiver 50 over the cellular transmission network 20. The cellular module 46 is further configured to communicate with and receive position data from an aGPS receiver 52, and to receive measurements from the external health sensors (e.g., sensors 18a-18n shown in FIG. 1) via a short-range Blue-Tooth transceiver 54 (or other equivalent short range transceiver such as a WiFi transceiver) or via a direct connection to one or more health sensors (e.g., the health sensors may be directly attached/coupled to the portable computing device 12a).

In addition to recording audio data for movement analysis, the cellular module 46 is further configured to permit direct voice communication between the user 16a and the PSAP (e.g. 9-1-1, an emergency response center, etc., not shown in the figures), a call center 30, first-to-answer systems 32 (e.g. a fire station, a police station, a physician's office, a hospital, etc.), or care givers and/or family 34 via a built-in speaker 58 and an amplifier 60. Either directly or via the distributed cloud computing system 14, the cellular module 46 is further configured to permit the user 16a to conduct a conference connection with one or more of a PSAP, the call center 30, the first-to-answer systems 32, and/or care givers and/or family 34. The cellular module 46 may receive/operate one or more input and output indicators 62 (e.g., one or more mechanical and touch switches (not shown), a vibrator, LEDs, etc.). The portable computing device 12a also includes an on-board battery power module 64.

The portable computing device 12a may also include one or more buttons. The buttons may allow a user to provide user input to the portable computing device 12a. For example, the user may press or push a button to initiate a voice call to one or more of a call center 30, first-to-answer systems 32 (e.g. a fire station, a police station, a physician's office, a hospital, etc.), or care givers and/or family 34. In another example, a user may use a button to answer questions during a voice call (e.g., push a button once for "yes" and push the button twice for "no"). In another example, the user may indicate that the portable computing device should start collecting data (e.g., datasets such as health data, audio data, location data, etc.) and/or send data to the distributed cloud computing system 14, using the buttons. In a further example, the user may also push the button to end a voice call and/or to cancel an outgoing call.

The portable computing device 12a may also include empty expansion slots and/or connectors (not shown) to collect readings from other sensors (i.e., an inertial measurement unit, a pressure sensor for measuring air pressure or attitude, a heart rate sensor, blood perfusion sensor, temperature sensor, glucose level sensor), etc. These other sensors may be coupled to the device via the expansion slots and/or connectors to provide additional datasets or information to the distributed cloud computing system 14. The portable computing device 12a, coupled with a sensor device, may be a health monitoring device (e.g., a device capable of measuring health related information of a user, such as heart rate, temperature, blood pressure, glucose level, etc.).

In one embodiment, the portable computing device 12a may include one or more magnetic elements (e.g., elements which generate a magnetic field, such as magnets) and one or more electrical contacts 62. The portable computing device 12a may couple with different sensors or external devices using the one or more magnetic elements and/or one or more electrical contacts 62. In one embodiment, the sensors or external devices may also include on or more magnetic elements. In one embodiment, the magnetic elements may be permanent or electromagnetic magnets. In another embodiment, the magnetic elements may be rare earth magnets or may be composed of a ferromagnetic material. Any combination of materials or magnets may be used in the portable computing device 12a and the external devices. For example, the portable computing device 12a may use electromagnetic magnets and the external devices may use permanent magnets. In another example, the portable computing device 12a may use rare earth magnets and the external device may use ferromagnetic materials.

In one embodiment, the magnetic elements of the sensors or external device may be positioned such that they align with the magnetic elements in the portable computing device 12a. In one embodiment, the magnetic elements in the portable computing device 12a and the magnetic elements in the external device may have opposite polarities. The different in polarities may cause a magnetic attraction between the magnetic elements on the portable computing device 12a and the magnetic elements on a sensor/external device. The magnetic attraction may cause the sensor/external device to couple and/or attach to the portable computing device 12a. In one embodiment, a sensor/external device may also include electrical contacts. In another embodiment, one magnetic element on the portable computing device 12a may have one polarity and a second magnetic element on the computing device 12a may have an opposite polarity, and one magnetic element on the sensor/external device may have one polarity and a second magnetic element on the sensor/external device may have the opposite polarity. For example, a left magnetic element on the portable computing device 12a may have one polarity and a right magnetic element portable computing device 12a may have an opposite polarity, and a left magnetic element on the sensor/external device may have the opposite polarity and a right magnetic element on the sensor/external device may have the one polarity. This may help prevent a user from attaching a sensor or external device incorrectly (e.g., prevent a user from trying to attach a sensor upside down) because the magnetic elements with opposite polarities will be magnetically attracted to each other and the magnetic elements with the same polarities will be magnetically repelled from each other.

When the sensor/external device is coupled/attached to the portable computing device 12a, the electrical contacts 62 on the portable computing device 12a may be positioned such that they align with the electrical contacts on the sensor/external device, when the sensor/external device is coupled/attached to the portable computing device 12a. The magnetic attraction between the magnetic elements on the portable computing device 12a and the magnetic elements on the sensor/external device may maintain an electrical connection between the electrical contacts on the portable computing device 12a and the electrical contacts on the sensor/external device (e.g., may maintain the electrical contacts in an electrically conductive relationship). In one embodiment, the portable computing device 12a and the sensor/external device may exchange data using one or more of the electrical contacts on the portable computing device and the sensor/external device. In another embodiment, the portable computing device 12a may provide power to the sensor/external device, using one or more of the electrical contacts on the portable computing device and the sensor/external device. For example, the portable computing device 12a may provide power to an external device containing a temperature sensor attached to the portable computing device 12a.

In one embodiment, the magnetic elements may be composed of electrical conductive materials, and may also be used as electrical contacts. For example, the magnetic elements may be used to couple a sensor and a portable computing device (via magnetic attraction) and may also be used to exchange data between the sensor and the portable computing device. In another example, the magnetic elements may be used to provide power to a sensor or to receive power from a power source.

In one embodiment, the portable computing device 12a may collect, gather, and/or obtain information using a variety of components. For example, the portable computing device 12a may obtain orientation and/or movement data (e.g., information about how a user who is wearing the portable computing device 12a has moved) using the accelerometer 40, the magnetometer 42, and/or the gyroscope 44. In another example, the portable computing device 12a may determine the location (e.g., location data, such as GPS coordinates) of the portable computing device 12a (and the user who is wearing or holding the portable computing device 12a) using the aGPS receiver 52. In a further example, the portable computing device may collect health data (e.g., heart rate, blood pressure, sugar levels, temperature, etc.) using sensors which may be attached to the portable computing device 12a and/or may communicate with the portable computing device 12a using the Bluetooth transceiver 54. In yet another example, the portable computing device 12a may obtain audio data (e.g., voice and/or sounds) using the microphone 48 or a plurality of microphones (now shown in the figures).

In one embodiment, the portable computing device 12a may obtain and/or generate datasets (e.g., orientation/movement data, health data, location data, audio data) using these components and may transmit these datasets to the distributed cloud computing system 14. In another embodiment, the portable computing device 12a may periodically transmit data sets to the distributed cloud computing system 14. For example, the portable computing device 12a may transmit the datasets once every 5 seconds, or once every 30 seconds. In another embodiment, the portable computing device 12a may transmit the datasets when certain criteria are met (e.g., when an accelerometer detects an acceleration above a certain threshold indicating a possible fall, or when the aGPS receiver determines that the portable computing devices has left a certain location). In a further embodiment, the portable computing device 12a may transmit datasets when a user input is received. For example, the portable computing device 12a may send the datasets when the user presses or pushes a button, in order to initiate a voice call.

In one embodiment, the portable computing device 12a may process the datasets, prior to providing the datasets to the distributed cloud computing system 14. For example, the portable computing device 12a may process motion and/or orientation data to make an initial determination as to whether a user event (e.g., a fall or some other accident) has occurred. The distributed cloud computing system 14 may further process the datasets, in addition to the processing performed by the portable computing device 12a. In another embodiment, the portable computing device 12a may provide the datasets to the distributed cloud computing system 14 without first processing the datasets, and may allow the distributed cloud computing system 14 to process the datasets. In one embodiment, the distributed cloud computing system 14 may have more processing power (e.g., more CPUs) and may be better able to process and/or analyze the datasets than the portable computing device 12a.

In one embodiment, the portable computing device 12 may be an electronic device such as a smart phone, a personal digital assistant (PDA), a tablet computer, a portable media player (e.g., n portable audio player), a digital media reader (e.g., an electronic book reader) or other portable computing device. It should be understood that in other embodiments, the electronic device may include a variety of other components including, but not limited to, other buttons, a touch screen, a keyboard or other input device, a digital camera, a video camera, etc.).

Figure 3:
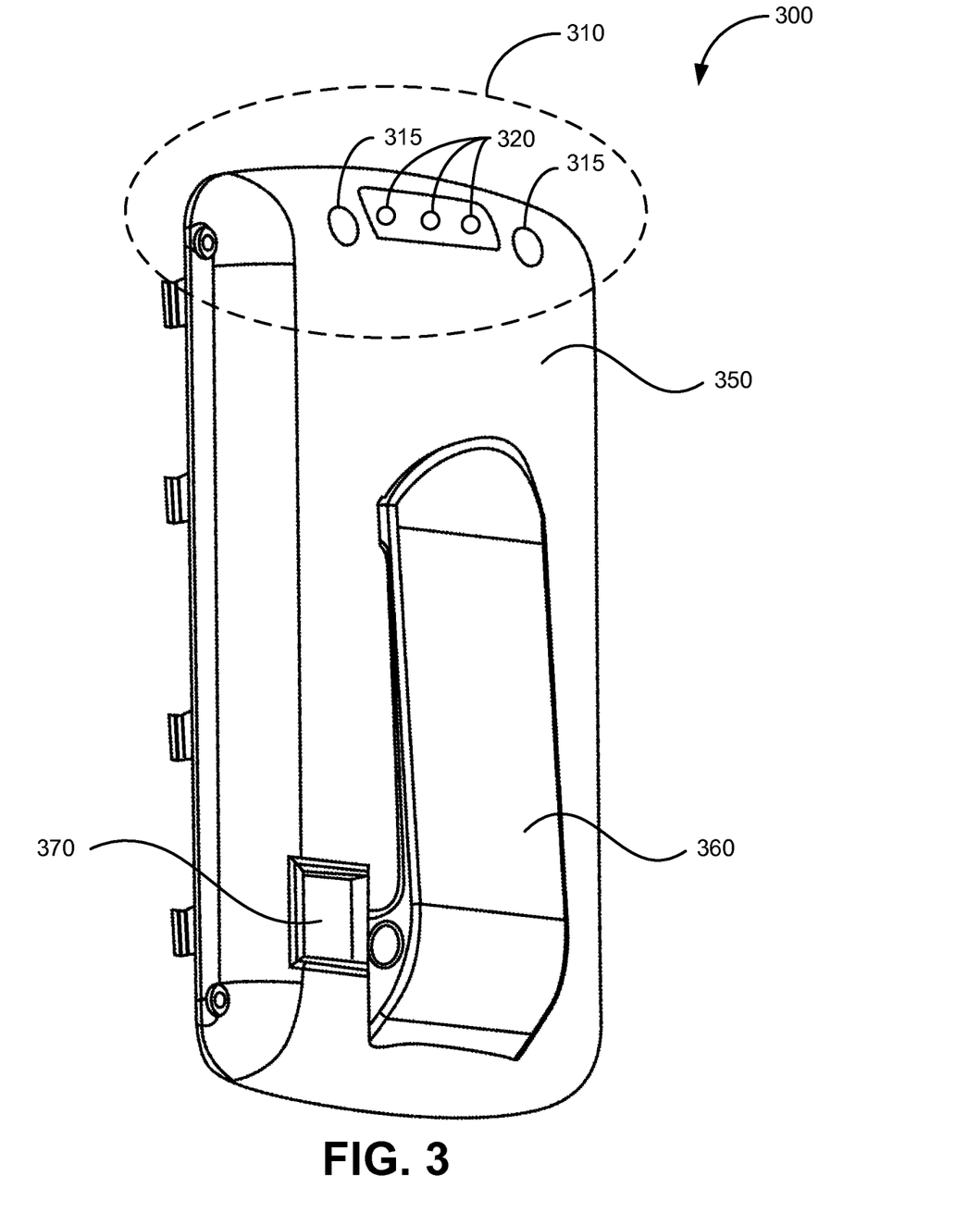
FIG. 3 is a perspective view of a portable computing device according to one embodiment.

FIG. 3 is a perspective view of a portable computing device 300 according to one embodiment. As discussed above, the portable computing device 300 may include, but is not limited to, a smart phone, a PDA, a portable media player, a cellular phone, a tablet computer, a portable computing device, etc.

The portable computing device 300 has an outer surface 350. The outer surface 350 of the portable computing device may comprise any combination of different materials including, but not limited to, plastics, polymers, rubber, composite materials, metal, metal alloys, thermoplastics (e.g., polycarbonate, and acrylonitrile butadiene styrene) etc. In one embodiment, the outer surface 350 may be constructed using injection molding and/or vacuum casting. In one embodiment, the portable computing device 300 includes a clip 360. The clip 360 may be used to attach (e.g., clip) the portable computing device 300 to an object such as a pocket, a belt, a waistband, etc. In other embodiments, the portable computing device 300 may not include the clip 360. For example, the portable computing device 300 may be a cellular phone, PDA, or a smart phone which does not include the clip 360. The portable computing device 300 may also include a digital camera 370. The digital camera 370 may be capable of capturing images (e.g., pictures) and/or videos.

The portable computing device 300 includes an upper portion 310. The upper portion 310 includes magnetic elements 315 (e.g., circular, rectangular, or different shaped magnets) and a one or more electrical contacts 320. As discussed in more detail in conjunction with FIGS. 5-11, the magnetic elements 315 may couple to corresponding magnetic elements on a charging device (e.g., an alternating current (AC) adaptor or a charging station/dock) or may couple to corresponding magnetic elements on an attachable electronic device (e.g., an attachable device containing a health sensor such as a temperature sensor or a heart rate sensor). Also as discussed in more detail in conjunction with FIGS. 5-11, the electrical contacts 320 may couple to corresponding electrical contacts on a charging device or my couple to corresponding electrical contacts on an attachable electronic device. In one embodiment, the portable computing device 300 may exchange data with the attachable electronic device and/or provide power to the attachable electronic device using one or more of the electrical contacts 320. In another embodiment, the portable computing device 300 may receive power to charge a battery within the portable computing device 300, using one or more of the electrical contacts 320.

Figure 4:
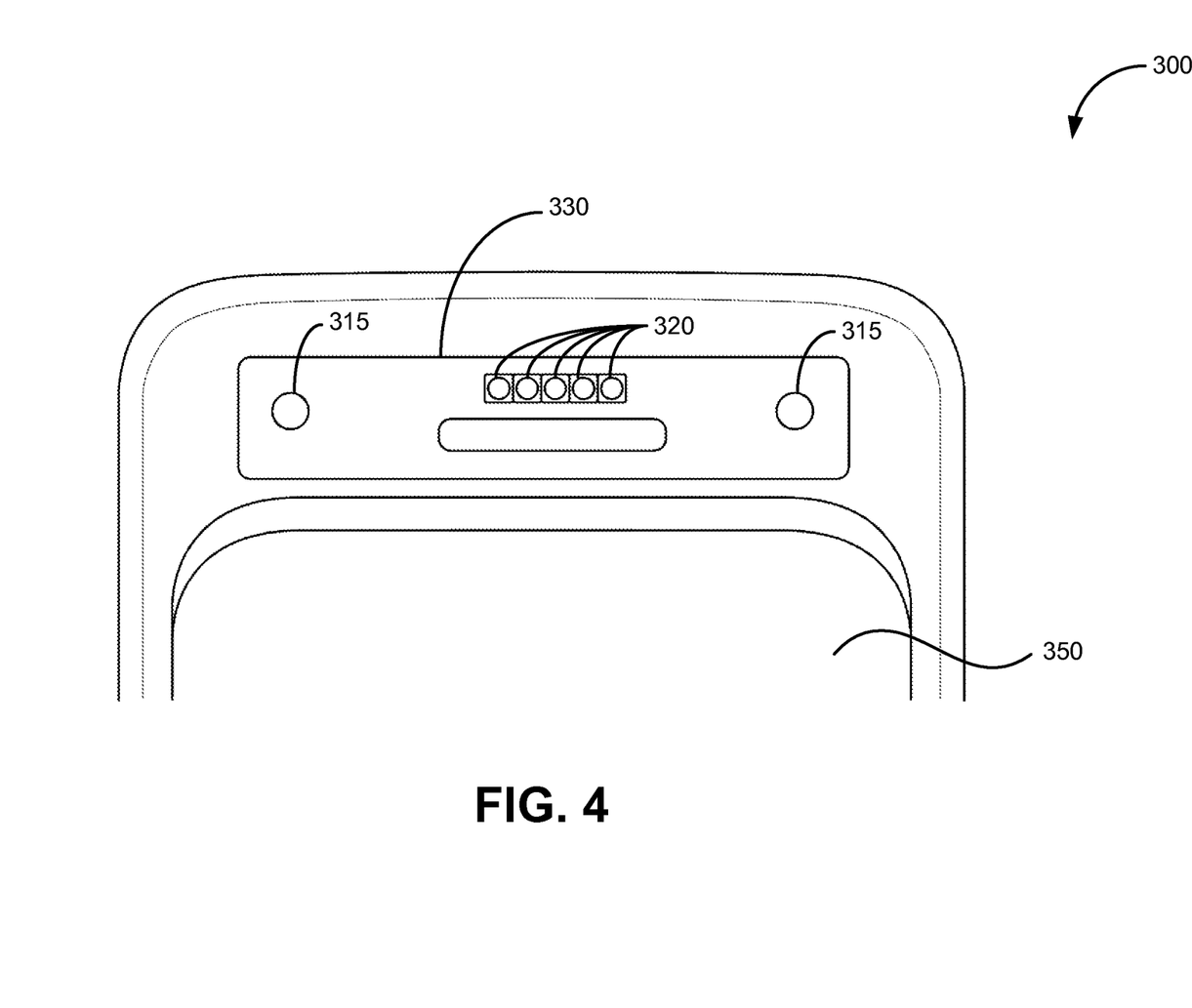
FIG. 4 is a close-up front view of the upper portion of the portable computing device from FIG. 1.

FIG. 4 is a close-up front view of the upper portion 310 of the portable device 300 from FIG. 1. As discussed above in conjunction with FIG. 3, the portable device 300 includes magnetic elements 315 (e.g., a set of magnetic elements 315) and electrical contacts 320 (e.g., a set of electrical contacts 320). The electrical contacts 320 are positioned between the magnetic elements 315 and are parallel to an upper edge of the portable computing device. It should be understood that in other embodiments, the magnetic elements 315 and the electrical contacts 320 may be positioned differently. For example, the electrical contacts 320 may be positioned above or below the magnetic elements 315. In another example, the magnetic elements 315 may be positioned between the electrical contacts 320. In a further example, the portable device 300 may include only one magnetic element. For example, the magnetic element may be a hollow rectangular or hollow circular shape and the electrical contacts may be positioned within the magnetic element.

The electrical contacts 320 and the magnetic elements 315 are positioned within a contact portion 330 in the outer surface 350 of the portable device 300. The contact portion 330 may be a portion on the outer surface 350 which may physically contact an outer surface of power source (e.g., an outer surface of a charging station or a power adaptor) and/or an outer surface of an attachable electronic device (e.g., an outer surface of a health sensor device). In one embodiment, the contact portion 330 may have a size and/or shape which is substantially similar to the size and/or shape of the outer surface of an outer surface of a attachable sensor device. In another embodiment, the contact portion 330 may be recessed within a housing or casing of the portable computing device 300, as discussed later in conjunction with FIGS. 5-11. It should be understood that the contact portion 330 may be any size and/or shape. For example, the contact portion 330 may be an oval/circular shape, instead of a rectangular/square shape. In another example, the contact portion 330 may have a trapezoidal shape.

Figure 5:
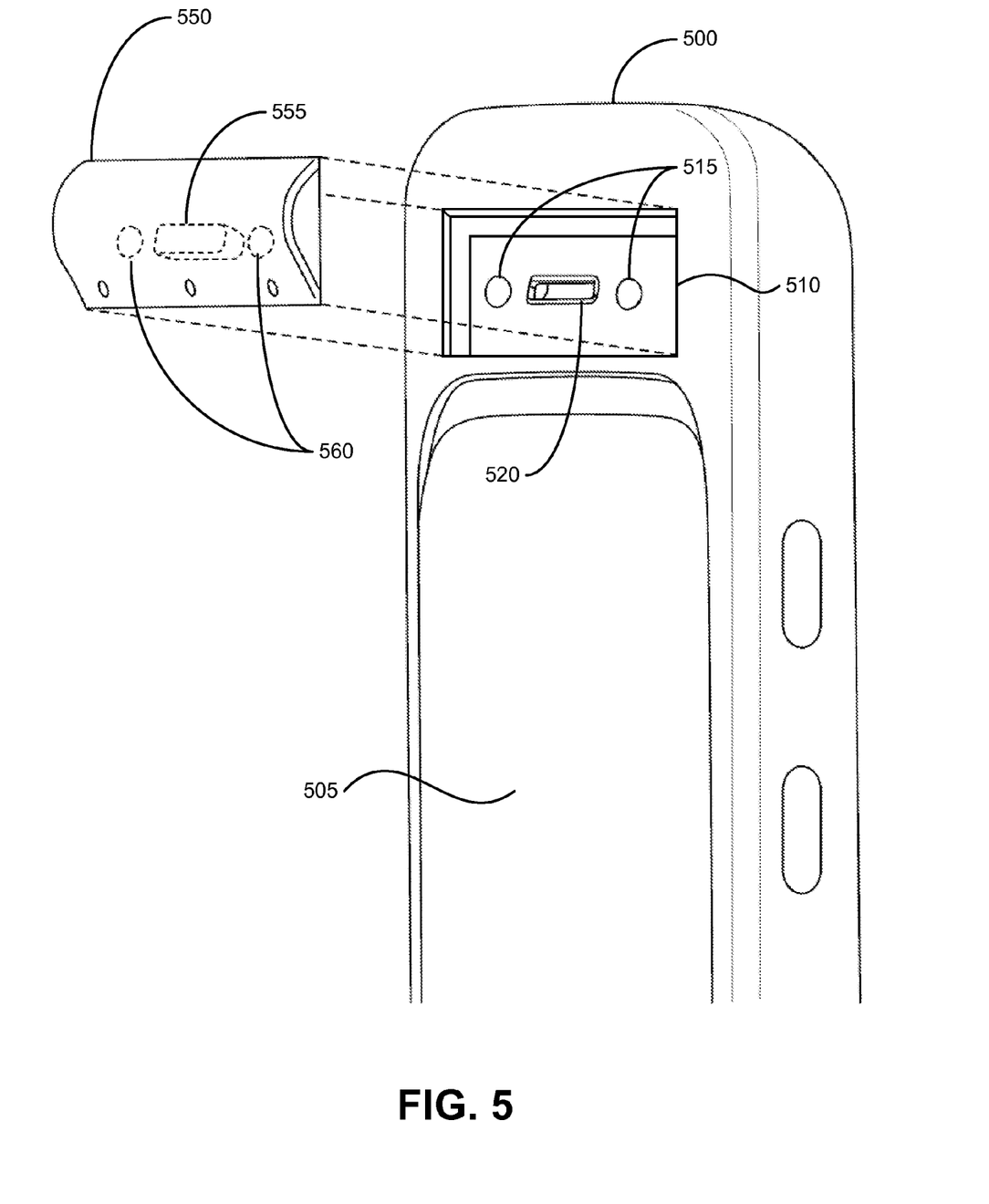
FIG. 5 is a perspective view of a portable computing device and an attachable electronic device, according to one embodiment.

FIG. 5 is a perspective view of a portable computing device 500 and an attachable electronic device 550, according to one embodiment. The portable computing device 500 includes an outer surface 505. The outer surface 505 includes a contact portion 510. The contact portion 510 is recessed within an outer housing (e.g., a plastic casing) of the portable computing device 500. The contact portion 501 includes magnetic elements 515 (e.g., magnets) and electrical contacts 520. The individual electrical contacts 520 are not shown in FIG. 5.

The attachable electronic device 550 includes a outer surface and the outer surface of the attachable electronic device 550 includes magnetic elements 560 and electrical contacts 555. The individual electrical contacts 555 are not shown in FIG. 5. The magnetic elements 560 and the electrical contacts 555 are positioned such that the magnetic elements 560 align with the magnetic elements 515 and the electrical contacts 555 align with the electrical contacts 520. In one embodiment, the size and shape of the outer surface of the attachable electronic device 550 are substantially similar to the size and shape of the contact portion 510. For example, as shown in FIG. 5, the outer surface of the attachable electronic device 550 has a rectangular shape similar in size to the rectangular shape of the contact portion 510 of the portable computing device 500. In one embodiment, the outer surface of the attachable electronic device 550 may fit within the recessed contact portion 510.

In one embodiment, the magnetic elements 515 may be "male" connection elements (e.g., connection elements which protrude from the outer surface 505 and the magnetic elements 560 may be "female" connection elements (e.g., connection elements which are recessed within the outer surface of the attachable electronic device 550. In another embodiment, the magnetic elements 515 may be "female" connection elements and the magnetic elements 560 may be "male" connection elements. In a further embodiment, the magnetic elements 515 may be flush with the surface of the contact portion 510 and the magnetic elements 560 may be flush with the outer surface of the attachable electronic device 550.

In one embodiment, the electrical contacts 520 may be "male" connection elements (e.g., connection elements which protrude from the outer surface 505 and the electrical contacts 555 may be "female" connection elements (e.g., connection elements which are recessed within the outer surface of the attachable electronic device 550. In another embodiment, the electrical contacts 520 may be "female" connection elements and the electrical contacts 555 may be "male" connection elements. In a further embodiment, the electrical contacts 520 may be flush with the surface of the contact portion 510 and the electrical contacts 555 may be flush with the outer surface of the attachable electronic device 550.

Figure 6:
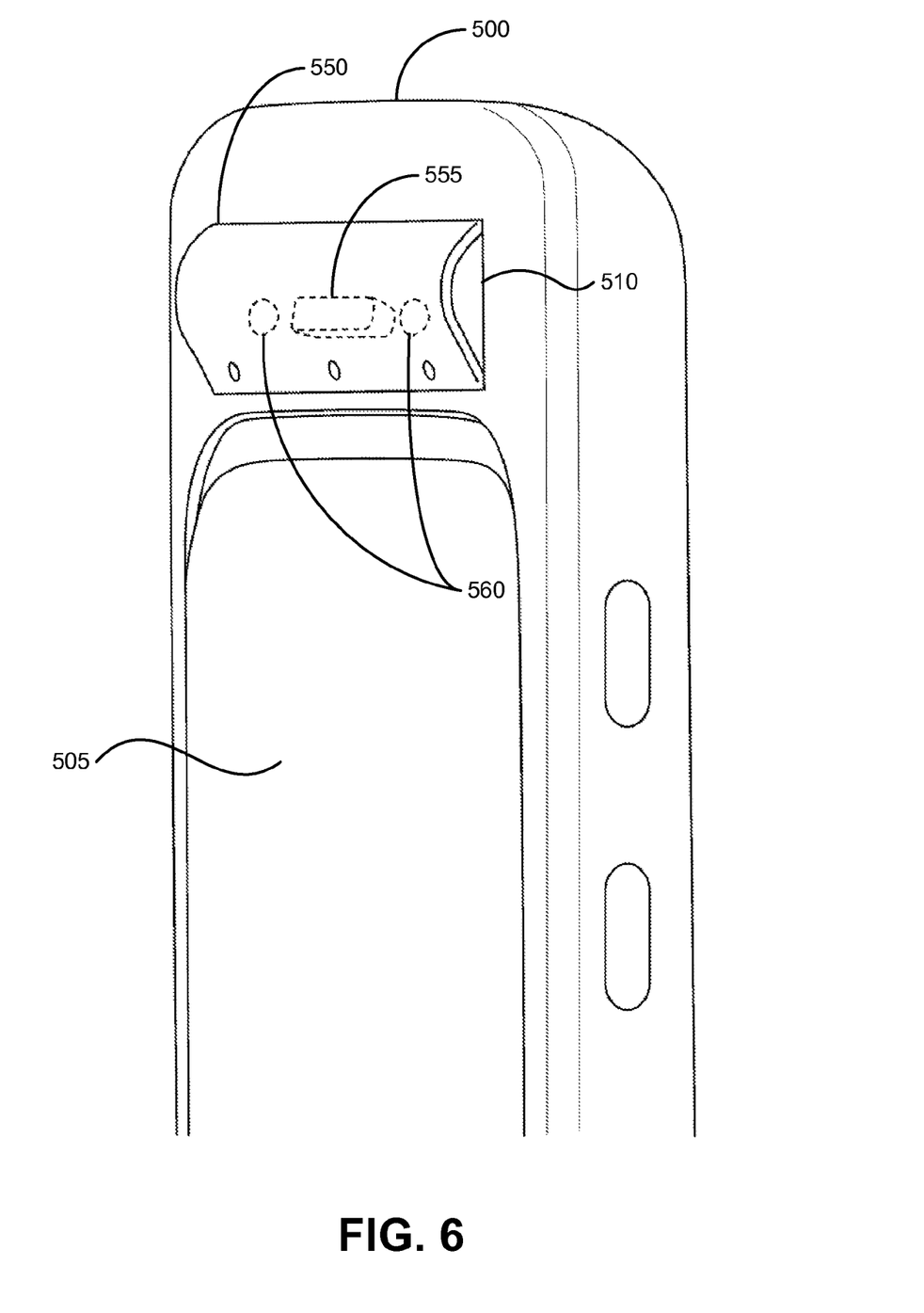
FIG. 6 is a perspective view of the portable computing device and the attachable electronic device of FIG. 5, according to another embodiment.

FIG. 6 is a perspective view of the portable computing device 500 and the attachable electronic device 550 of FIG. 5, according to another embodiment. The attachable electronic device 550 is attached to the portable computing device 500 at the contact portion 510. In one embodiment, the contact portion 510 is recessed and a outer surface of the electronic device 550 fits within the recessed contact portion 510. The recessed contact portion 510 may allow the electronic device 550 to be properly aligned such that the magnetic elements 560 and the electrical contacts 555 line up with the magnetic elements 515 and electrical contacts 520 of the portable computing device (not shown in FIG. 6). In another embodiment, the contact portion 510 may not be recessed, and may be flush with the outer surface 505 of the portable computing device 500. The attachable electronic device 550 may be attached to the portable computing device 500 using the magnetic elements 560 and 515.

As shown in FIG. 6, the attachable electronic device 550 is coupled/attached to the portable computing device 500 using the magnetic elements 560 and the magnetic elements 515. As the attachable electronic device 550 is brought into proximity to the contact portion 510, the magnetic attraction between the magnetic elements 515 and the magnetic elements 560 cause the attachable electronic device 550 to couple/attach (e.g., to snap onto) the portable computing device 500. Referring back to FIG. 5, the magnetic elements 560 and the magnetic elements 515 are aligned with each other when the attachable electronic device 550 is attached to the portable computing device 500. Similarly, the electrical contacts 520 and the electrical contacts 555 are also aligned with each other when the attachable electronic device 550 is attached to the portable computing device 500.

In one embodiment, the attachable electronic device 550 may exchange data with (e.g., communicate with) the portable computing device 500 using one or more of the electrical contacts 520 and 555. For example, the attachable electronic device 550 may be a device containing one or more health sensors which measures or determines health related information (e.g., blood pressure, heart rate, temperature, etc., of a user). The attachable electronic device 550 may provide data (e.g., heart rate) to the portable computing device 500 using one of the electrical contacts 520 and one of the electrical contacts 555. In another embodiment, the portable computing device 500 may provide power to the attachable electronic device 550 using one or more of the electrical contacts 520 and 555. For example, the portable computing device 500 may provide power to the attachable electronic device 550 in order to provide power for the operation of the attachable electronic device 550.

Figure 7:
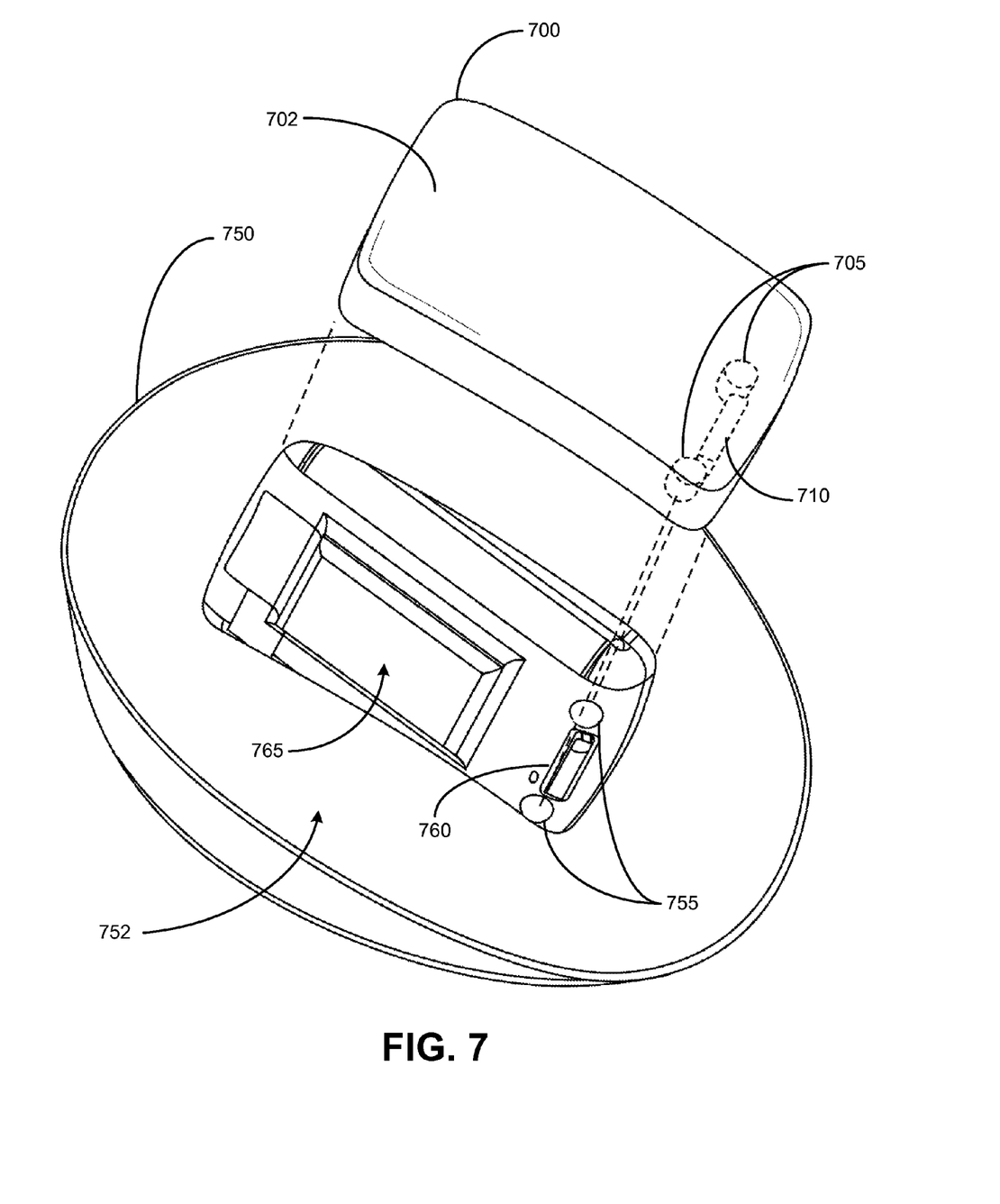
FIG. 7 is a perspective view of a portable computing device and a power source, according to one embodiment.

FIG. 7 is a perspective view of a portable computing device 700 and a power source 750, according to one embodiment. The portable computing device 700 includes an outer surface 702 which includes a contact portion (not shown in FIG. 7). The contact portion includes magnetic elements 705 (e.g., magnets) and electrical contacts 710. The individual electrical contacts 710 are not shown in FIG. 7. The power source 750 may be a charging station, a charging base, a charging cradle, etc. In other embodiments, the power source 750 may be an AC adaptor (e.g., a plug) or some other type of connection which connects to the contact portion of the portable computing device 700.

The power source 750 includes an upper surface 752 and recess 756. The power source 750 includes magnetic elements 755 and electrical contacts 760. The individual electrical contacts 760 are not shown in FIG. 7. The magnetic elements 755 and the electrical contacts 760 are positioned such that the magnetic elements 755 align with the magnetic elements 760 and the electrical contacts 705 align with the electrical contacts 710. The power source 750 may provide power (e.g., an electrical current such as an AC or direct current (DC)) to the portable computing device 700 using one or more of the electrical contacts 710 and 760. The portable computing device 700 may charge a battery (or other type of power storage device) using the power provided by the power source 750. In one embodiment, the size and shape recess 765 are substantially similar to the size and shape of the outer surface of the portable computing device 700. In one embodiment, the outer surface of the portable computing device 700 may fit within the recess 756 (e.g., the outer surface of the portable computing device 700 may substantially conform to the surface of the recess 765).

As discussed above in conjunction with FIG. 5, the magnetic elements 705 and 755, and the electrical contacts 710 and 760 may be male/female connection element source may be flush to the surfaces of the portable computing device 700 and the power source 750.

Figure 8:
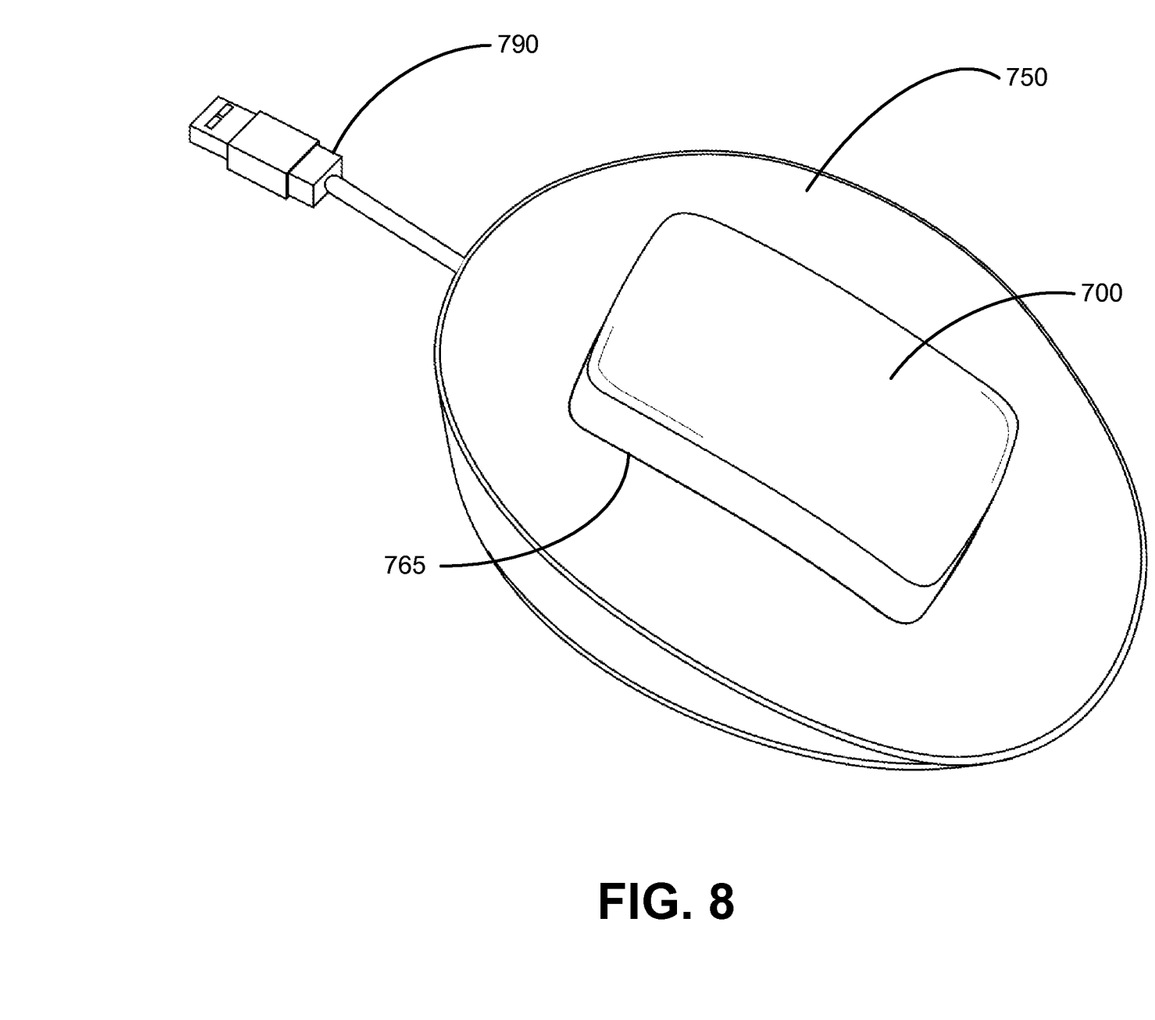
FIG. 8 is a perspective view of the portable computing device and the power source of FIG. 7, according to another embodiment.

FIG. 8 is a perspective view of the portable computing device 700 and the power source 750 of FIG. 7, according to another embodiment. As shown in FIG. 8, the portable computing device 700 is coupled to the power source 750. The outer surface of the portable computing device 700 fits within the recess 765 of the power source 750. In one embodiment, a magnetic attraction between magnetic pads 705 on the portable computing device and the magnetic pads 755 on the power source may maintain an electrical connection between the electrical contacts on the portable computing device 700 and the electrical contacts on the power source 750 (e.g., may maintain two or more of the electrical contacts 710 and 760 in an electrically conductive relationship). In one embodiment, gravity may also help maintain the electrical connection between the electrical contacts on the portable computing device 700 and the electrical contacts on the power source 750. In another embodiment, gravity may assist a user in placing the portable computing device 700 into position, in order to charge the portable computing device 700 (e.g., a charging position). As shown in FIG. 8, the power source 750 has a downward sloping surface. As the portable computing device 700 is placed within the recess 765, the portable computing device 700 may slide downwards within the recess 765 due to gravitational and/or magnetic forces, which may help maintain the electrical connection between the electrical contacts on the portable computing device 700 and the electrical contacts on the power source 750. In one embodiment, the gravitational and/or magnetic forces may allow the portable computing device 700 to be positioned such that the portable computing device can be charged by the power source 750. For example, a user may not completely place the portable computing device 700 into the recess 765. However, due to gravity, the portable computing devices may slide down towards the magnetic contacts 755. In addition, the magnetic attraction between the magnetic elements 755 and 705 may further cause the portable computing device 700 to slide into a position (e.g., a charging position) such that the portable computing device 700 can be charged by the power source 750.

In one embodiment, the power source 750 may be coupled to an external computing device (e.g., a desktop computer or a laptop computer) via an external connector 790 (e.g., via a universal serial bus (USB) connector). The power source 750 may also facilitate the exchange of data between the portable computing device 700 and the external computing device. For example, the power source 750 may transmit data received from the portable computing device 700 to the external computing device. In another example, the power source 750 may transmit data received from the external computing device to the portable computing device 700.

Figure 9:
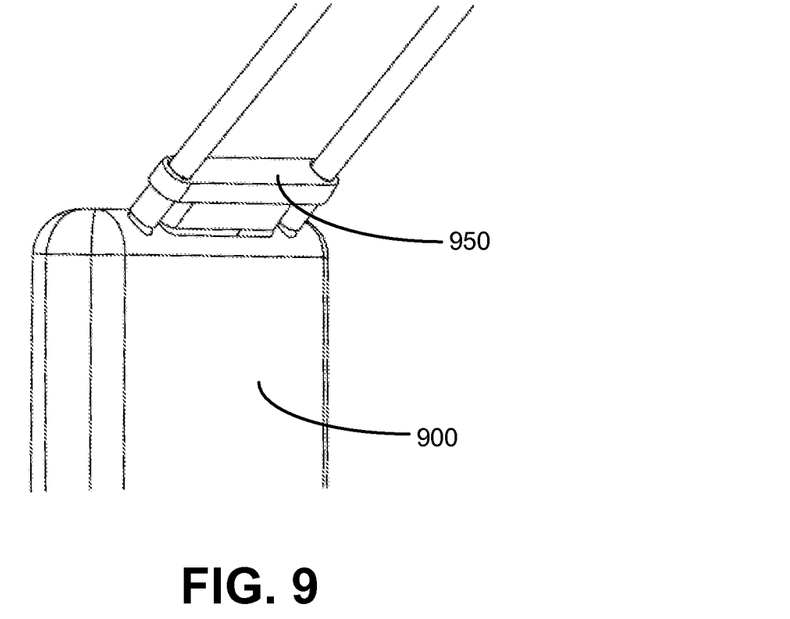
FIG. 9 is a perspective view of a portable computing device and an attachment.

FIG. 9 is a perspective view of a portable computing device 900 and an attachment 950. The computing device 900 and the attachment 950 may each include a set of magnetic elements (not shown in FIG. 9) and a set of electrical contacts (not shown in FIG. 9). The magnetic attraction between the sets of magnetic elements may maintain an electrical connection between the sets of electrical contacts. The attachment 950 may include, but is not limited to, an antenna, a connection to an external computing device, an attachable computing device (such as a health sensor or other type of sensor), etc.

Figure 10:
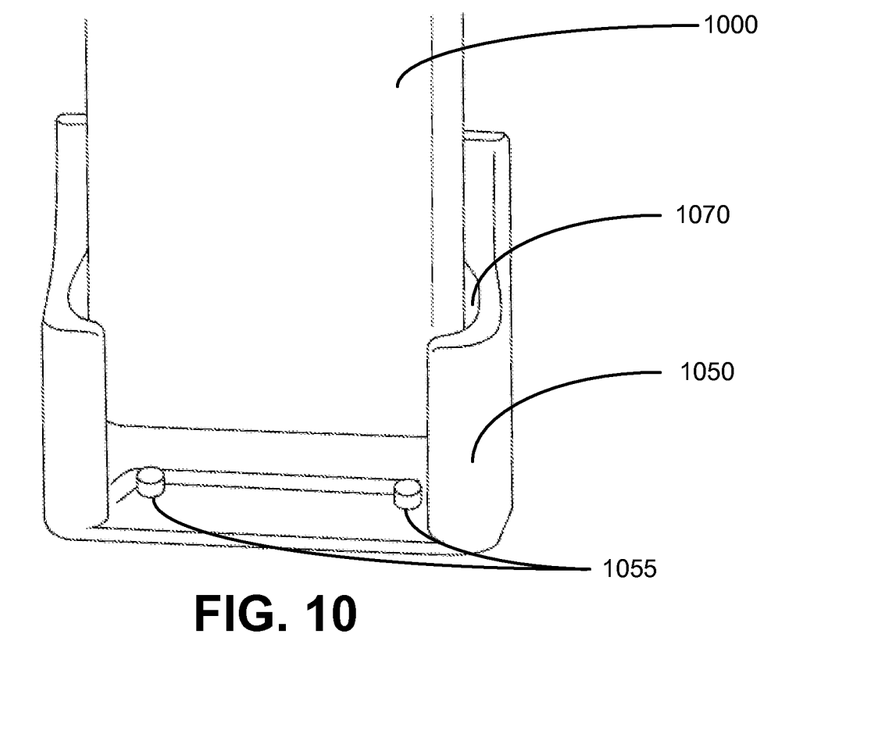
FIG. 10 is a perspective view of a portable computing device and an power source.

FIG. 10 is a perspective view of a portable computing device 1000 and power source 1050. The power source 1050 includes magnetic elements 1055 which may be aligned with magnetic elements in the portable computing device 1000 (not shown in FIG. 10). As shown in FIG. 10, the computing device 1000 fits within a groove or recess 1070 within the power source 1050 and may slide into the power source 1050. The magnetic elements 1055 may be magnetically attracted to magnetic elements in the portable computing device 1000.

The portable computing device 1000 may slide into a position to charge the portable computing device 1000 based on gravitational and/or magnetic forces, as discussed above in conjunction with FIG. 8.

Figure 11:
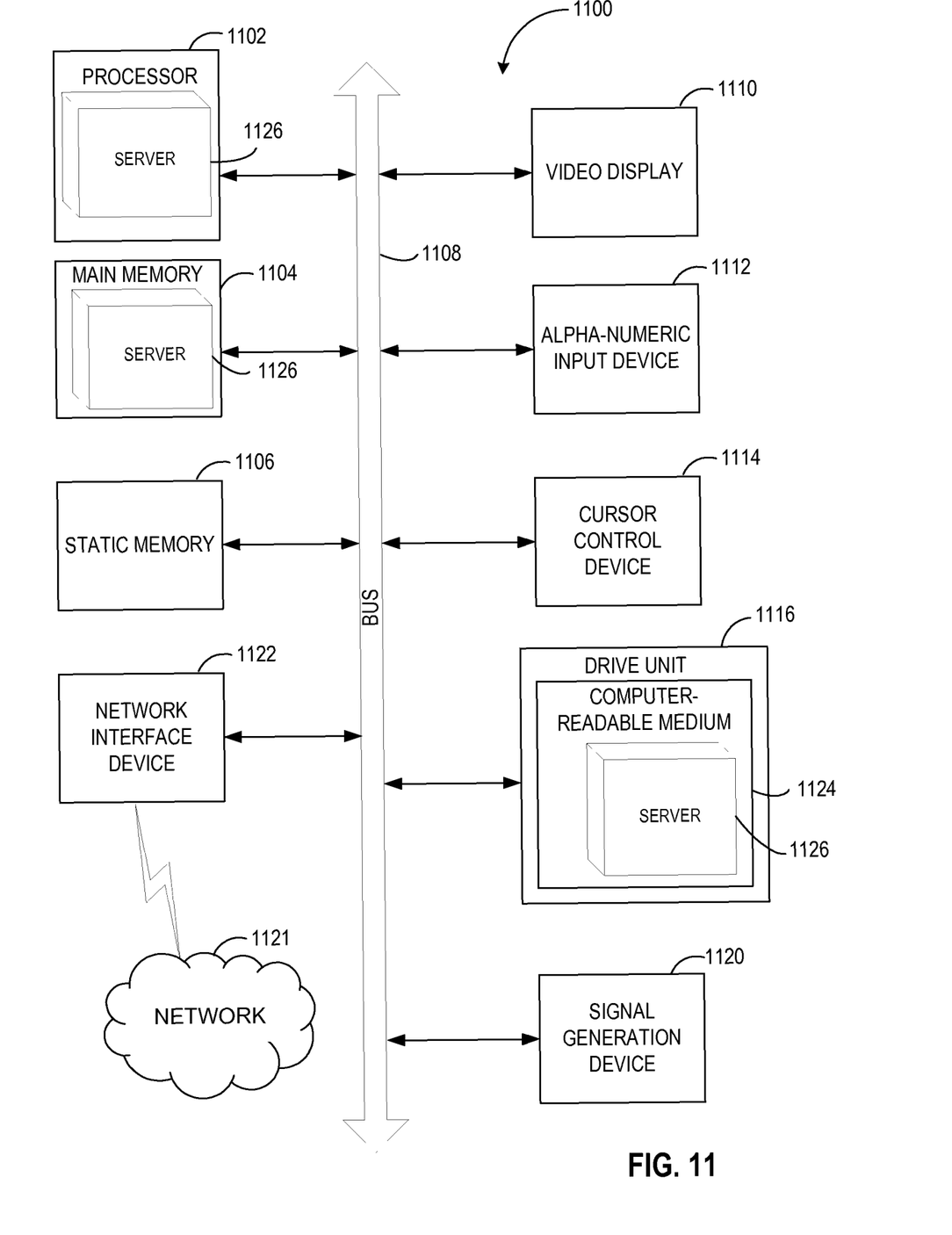
FIG. 11 is a block diagram of an exemplary computer system that may perform one or more of the operations described herein.

FIG. 11 illustrates a diagrammatic representation of a machine in the exemplary form of a computer system 1100 within which a set of instructions, for causing the machine to perform any one or more of the methodologies discussed herein, may be executed. In alternative embodiments, the machine may be connected (e.g., networked) to other machines in a LAN, an intranet, an extranet, or the Internet. The machine may operate in the capacity of a server or a client machine in client-server network environment, or as a peer machine in a peer-to-peer (or distributed) network environment. The machine may be a personal computer (PC), a tablet PC, a set-top box (STB), a Personal Digital Assistant (PDA), a cellular telephone, a smart phone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The exemplary computer system 1100 includes a processing device (processor) 1102, a main memory 1104 (e.g., read-only memory (ROM), flash memory, dynamic random access memory (DRAM) such as synchronous DRAM (SDRAM) or Rambus DRAM (RDRAM), etc.), a static memory 1106 (e.g., flash memory, static random access memory (SRAM), etc.), and a data storage device 1116, which communicate with each other via a bus 1108.

Processor 1102 represents one or more general-purpose processing devices such as a microprocessor, central processing unit, or the like. More particularly, the processor 1102 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor 1102 may also be one or more special-purpose processing devices such as an application specific integrated circuit (ASIC), a field programmable gate array (FPGA), a digital signal processor (DSP), network processor, or the like. The processor 1102 is configured to execute instructions 1126 for performing the operations and steps discussed herein.

The computer system 1100 may further include a network interface device 1122. The computer system 1100 also may include a video display unit 1110 (e.g., a liquid crystal display (LCD) or a cathode ray tube (CRT)), an alphanumeric input device 1112 (e.g., a keyboard), a cursor control device 1114 (e.g., a mouse), and a signal generation device 1120 (e.g., a speaker). In one embodiment, the video display 1110, the alpha-numeric devices 1112 and the cursor control device 1114 may be combined into a single device, such as a touch screen.

The data storage device 1116 may include a computer-readable storage medium 1124 on which is stored one or more sets of instructions 1126 (e.g., software) embodying any one or more of the methodologies or functions described herein. The instructions 1126 may also reside, completely or at least partially, within the main memory 1104 and/or within the processor 1102 during execution thereof by the computer system 1100, the main memory 1104 and the processor 1102 also constituting computer-readable storage media. The instructions 1126 may further be transmitted or received over a network 1121 via the network interface device 1122.

In one embodiment, the instructions 1126 may include instructions to execute a server such as the telephony server 22, the real time data monitoring server 36, and/or the web server 28 of FIG. 1. While the computer-readable storage medium 1124 is shown in an exemplary embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

In the foregoing description, numerous details are set forth. It will be apparent, however, to one of ordinary skill in the art having the benefit of this disclosure, that the present disclosure may be practiced without these specific details. In some instances, well-known structures and devices are shown in block diagram form, rather than in detail, in order to avoid obscuring the present disclosure.

Some portions of the detailed description have been presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "initiating", "identifying", "receiving", "analyzing", "routing," "monitoring", or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

The present disclosure also relates to an apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions.

Reference throughout this specification to "one embodiment" or "an embodiment" means that a particular feature, structure, or characteristic described in connection with the embodiment is included in at least one embodiment. Thus, the appearances of the phrase "in one embodiment" or "in an embodiment" in various places throughout this specification are not necessarily all referring to the same embodiment. In addition, the term "or" is intended to mean an inclusive "or" rather than an exclusive "or." Moreover, the words "example" or "exemplary" are used herein to mean serving as an example, instance, or illustration. Any aspect or design described herein as "exemplary" is not necessarily to be construed as preferred or advantageous over other aspects or designs. Rather, use of the words "example" or "exemplary" is intended to present concepts in a concrete fashion.

It is to be understood that the above description is intended to be illustrative, and not restrictive. Many other embodiments will be apparent to those of skill in the art upon reading and understanding the above description. The scope of the disclosure should, therefore, be determined with reference to the appended claims, along with the full scope of equivalents to which such claims are entitled.

What is claimed is:

1. A health monitoring device comprising:
   a portable computing device having an outer surface comprising a recessed contact portion that is recessed within the outer surface and configured to receive a sensor device, the sensor device comprising a housing shaped to fit at least partially within the recessed contact portion, wherein the recessed contact portion comprises:
   a first set of magnetic elements, wherein the sensor device is attachable to the portable computing device using the first set of magnetic elements of the recessed contact portion and a second set of magnetic elements disposed on the housing of the sensor device;
   a first electrical contact configured to provide power to the sensor device; and
   a second electrical contact configured to exchange data with the sensor device.

2. The health monitoring device of claim 1, wherein the sensor device comprises a health sensor.

3. The health monitoring device of claim 1, wherein the first electrical contact is further configured to receive an electrical current from a power source.

4. The health monitoring device of claim 1, wherein each magnetic element in the first set of magnetic elements is positioned within the recessed contact portion, and wherein the recessed contact portion comprises a size and shape substantially similar to the housing of the sensor device.

5. The health monitoring device of claim 1, wherein each of the first electrical contact and the second electrical contact comprise a circular shape or a rectangular shape.

6. The health monitoring device of claim 1, wherein the first set of magnetic elements is magnetically attracted to the second set of magnetic elements disposed on the sensor device, and wherein the magnetic attraction maintains an electrical connection between the second electrical contact and a third electrical contact disposed on the sensor device.

7. The health monitoring device of claim 6, wherein health data is transmitted via the electrical connection between the second electrical contact and the third electrical contact.

8. The health monitoring device of claim 3, wherein the power source comprises a recessed portion having a size and shape substantially similar to a portion of the outer surface of the portable computing device.

9. The health monitoring device of claim 3, wherein the first set of magnetic elements is magnetically attracted to a third set of magnetic elements on the power source and wherein the power source provides an electrical current to the portable computing device via the first electrical contact.

10. The health monitoring device of claim 1, wherein an edge of the recessed contact portion is substantially parallel with an edge of the portable computing device.

11. The health monitoring device of claim 1, wherein the first set of magnetic elements, the first electrical contact, and the second electrical are all parallel to an edge of the portable computing device.

12. The health monitoring device of claim 1, wherein the health monitoring device is configured to transmit sensor data received from the sensor device to a server.

13. The health monitoring device of claim 1, wherein the portable computing device comprises internal sensors configured to generate sensor data, and wherein the health monitoring device is configured to transmit the sensor data to a server.

14. The health monitoring device of claim 1, wherein the sensor device further comprises a third electrical contact and a fourth electrical contact, wherein the first set of magnetic elements is aligned with the second set of magnetic elements, wherein the first electrical contact is aligned with the third electrical contact and the second electrical contact is aligned with the fourth electrical contact.

15. The health monitoring device of claim 14, wherein the third electrical contact is configured to receive power from the portable computing device and wherein the fourth electrical contact is configured to exchange data with the portable computing device.

16. The health monitoring device of claim 3, wherein the power source is coupled to an external computing device, and the health monitoring device is configured to exchange data with the external computing device via the power source.

17. The health monitoring device of claim 12, further comprising a wireless communication interface configured to transmit the sensor data to the server.

18. The health monitoring device of claim 3, wherein the portable computing device is positioned in a charging position on the power source using one or more of a gravitational force or a magnetic force between the first set of magnetic elements and the second set of magnetic elements.

19. The health monitoring device of claim 1, wherein a depth of the recessed contact portion is such that all of the housing of the sensor device fits within the recessed contact portion.

20. The health monitoring device of claim 1, wherein the first set of magnetic elements are arranged in a linear fashion within the recessed contact portion.

* * * * *